United States Patent [19]
Rutner et al.

[11] Patent Number: 5,248,590
[45] Date of Patent: Sep. 28, 1993

[54] SURFACE MODIFIED LIPOSOMES

[75] Inventors: Herman Rutner, Hackensack; Josephine D. Readio, Sparta; Leslie Oppenheimer, Kinnelon, all of N.J.

[73] Assignee: Becton, Dickinson and Company, Franklin Lakes, N.J.

[21] Appl. No.: 333,937

[22] Filed: Jul. 22, 1991

[51] Int. Cl.$^5$ .................. C12Q 1/28; G01N 33/544; G01N 33/547

[52] U.S. Cl. ....................... 435/5; 435/419; 435/975; 435/970; 436/528; 436/532; 436/829; 436/807; 436/808; 422/56; 422/58; 422/61

[58] Field of Search ............. 435/5, 7.9, 810, 962, 435/28; 436/528, 823, 829, 532, 92, 120

[56] References Cited

U.S. PATENT DOCUMENTS

| | | | |
|---|---|---|---|
| 4,429,008 | 1/1984 | Martin et al. | 428/402.2 |
| 4,743,560 | 5/1988 | Campbell et al. | 436/501 |
| 4,891,324 | 1/1990 | Pease et al. | 436/519 |
| 4,948,590 | 8/1990 | Hawrot et al. | 424/450 |

FOREIGN PATENT DOCUMENTS 0248621 1/1987 European Pat. Off. .

OTHER PUBLICATIONS

Bredehorst et al., Biochemistry, 25, 5693 (1986).
Martin et al., *Macromolecules as Drugs and as Carriers for Biologically Active Molecules*, New York Academy of Sciences, 446, 443, (1985).

Primary Examiner—Esther L. Kepplinger
Assistant Examiner—Nancy J. Parsons
Attorney, Agent, or Firm—Richard E. Brown

[57] ABSTRACT

A liposome reagent encapsulating a molecule to be targeted to a body site or used as an assay reporter has a ligand and a sulfonate-containing group on the liposome surface. Preferred ligands are antibodies or antibody fragments and preferred encapsulants are enzymes or dyes. In the most preferred reagents, the antibody and sulfonate-containing group are covalently bonded to the liposome surface through a connecting group which includes a succinimidyl group resulting from addition of the ligand or sulfonate-containing group to a maleimidyl group. The invention includes a kit of materials for performing an assay using the reagent of the invention as the tracer.

25 Claims, 1 Drawing Sheet

SURFACE MODIFIED LIPOSOMES

BACKGROUND OF THE INVENTION

1. Field of the Invention

This invention relates to liposomes, and more particularly relates to ligand linked liposomes having a surface chemically modified to provide enhanced performance as immunoassay reagents or as site directed carriers of therapeutic agents.

2. Background of the Invention

In recent years, liposomes have been extensively studied as reagents for immunoassay and as carriers of therapeutic agents. When used in an immunoassay, a liposome generally encapsulates a reporter molecule, such as a dye or an enzyme, and is complexed with a ligand, usually an antigen or antibody. The liposome-ligand complex is often referred to as the assay tracer. In a sandwich assay the tracer is a loaded liposome-antibody complex which binds noncompetitively to the assay analyte bound to a capture antibody. In a competitive assay, the tracer is a complex of the loaded liposome with the analyte, and the complex and the free analyte compete for a limited number of binding sites on the capture antibody.

When used as a carrier for a therapeutic agent, the liposome is covalently conjugated to a site-directed antiligand, usually an antibody specific for an antigen associated with the site. In this way, the therapeutic agent-carrier complex is transported to the intended site of action.

Much research has been directed to suitable methods for forming the liposome ligand complex. In one method, the liposomes and ligand are maintained in contact whereby the hydrophobic portion of the ligand nonspecifically associates with hydrophobic components of the liposome. This absorption method has not achieved widespread use because the stability of the complex may be insufficient for the intended purpose leading to dissociation and/or leakage of the dye or therapeutic agent from the liposome.

A generally suitable method for forming a more stable liposome complex is by covalent bonding of the ligand to a reactive constituent of the liposome membrane. The covalent bond may be formed either before or preferably after formation of the liposomes. In the preferred and generally used method, functional groups on the liposome and the ligand are joined by a heterobifunctional spacer molecule. One of the functional groups forms a covalent bond with a reactive group on the surface of the liposome. The second functional group forms a covalent bond with a reactive group, usually a thiol group, on the ligand.

Martin et al., in U.S. Pat. No. 4,429,008 discloses liposomes conjugated to a variety of spacer moieties terminating in thiol-reactive functional groups projecting outwardly from the liposome surface. The thiol reactive groups react with thiol groups of ligands, such as antigens and antibodies, to covalently attach the ligands to the lipsomes via stable thioether bonds. This disclosure makes no provision for unreacted thiol-reactive groups which may react with other nucleophilic groups in the assay environment.

Published European patent Application No. 248,621 to Hatoh et al. discloses a liposome-ligand complex which includes a group which blocks any thiol reactive groups on the liposome which are not conjugated to the ligand. The blocking group may be a sulfhydryl containing reducing agent such as cysteine, mercaptoethanol or dithiothreitol (DTT), or an amino group containing substance such as glycine, serine or TRIS.

Bredehorst et al., Biochemistry 25, 5693 (1986), discusses the problem of liposome stability during coupling of Fab fragments to liposomes containing N-[4 (p-maleimidophenyl)butyryl]phosphatidylethanolamine (MPB-PE) wherein the maleimido group is thiol reactive. It is reported that stability is high if the mole percentage of MPB PE is 2.5 or lower whereas 5.0% causes release of 95% of an encapsulated fluorescein dye.

A further problem often encountered during or after coupling of thiolated ligands to thiol reactive liposomes is aggregation of the liposomes. Martin et al. in *Macromolecules as Drugs and as Carriers for Biologically Active Molecules*, New York Academy of Sciences, 446, 443 (1985), discloses that the problem of aggregation of liposomes is significantly reduced when the liposomal membrane contains from 10 to 30% of phosphatidylglycerol. The same authors note that an approach to preventing or reversing liposome aggregation is to lower the ion strength of the coupling medium.

The above disclosures have contributed to overcoming the problems of liposome leakage, loss of ligand and reversible aggregation during storage or use but have not provided a satisfactory solution to the problem of irreversible aggregation due to liposome fusion, protein-protein or protein-liposome interactions. The present invention is directed to solution of this problem.

SUMMARY OF THE INVENTION

A reagent which may be used for targeting a therapeutic agent to a body site or as a tracer in an assay includes a liposome having particular groups on the surface and encapsulating the therapeutic agent or a reporter molecule for the assay. One of the surface groups is a ligand, preferably an antigen or antibody covalently bound to the surface by reacting a thiol group of the ligand with a thiol reactive group on the surface of the liposome. A second surface group has an anionic sulfonate functionality and is introduced onto the liposome surface by reacting particular sulfite or sulfonate precursor molecules with thiol-reactive groups which did not react with the ligand.

In a preferred reagent, the ligand is an antibody having a free thiol group and the liposome has surface amino groups covalently conjugated to a connecting group which includes the thiol-reactive group. In particularly preferred reagents, the thiol-reactive group is a maleimidyl group conjugated to the amino group by a carboxyl-containing linking group. The maleimidyl group, on reaction with the thiol containing ligand or the sulfonate precursor is converted to a succinimidyl group.

Preferred sulfonate precursor molecules are sulfite ion, bisulfite ion and mercaptoalkyl sulfonic acids or salts thereof.

The invention includes a kit of materials for performing an assay using the reagent of the invention as a tracer in the assay.

Liposome reagents are generally used as a suspension of submicron-sized particles in an aqueous medium. A problem well known to those skilled in the art is the tendency of such liposomes to aggregate (also known in the art as flocculation or clumping), reversibly or irreversibly. It is further well-known that aggregation or leakage are particular problems with liposomes in which maleimide groups make up five or greater mole percent by weight of the membrane composition.

The liposome reagents of the invention provide enhanced assay sensitivity as compared with prior art liposomes using neutral or amphoteric blocking agents. Further, the reagent of the invention provides the unexpected added advantages of greater stability, less stickiness during column purification and significantly decreased irreversible aggregation on prolonged storage. Avoidance of aggregation during storage is a valuable improvement for reagents which often experience considerable shelf- time prior to use. It is believed, although not yet substantiated, that the decreased aggregation shown by the reagents of the invention is due to the high negative charge provided by the anionic sulfonate group. In addition, unlike conventional cysteine and mercaptoacetic acid blocked liposome reagents, the anionic liposomes of this disclosure remain fully charged above pH 3, a critical parameter when the reagent of the invention is to be used in an assay performed in the usual pH range of about 6 to 8, or as a targeting agent in the bloodstream.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The reagent of the invention is a liposome functionalized with particular surface groups and having an encapsulated molecule so that the reagent may be used in assay of an analyte or in targeting of a therapeutic agent. (In the following discussion of the drawings, elements which correspond to elements previously described are given the same base number followed by a lower case letter.)

Figure 1:
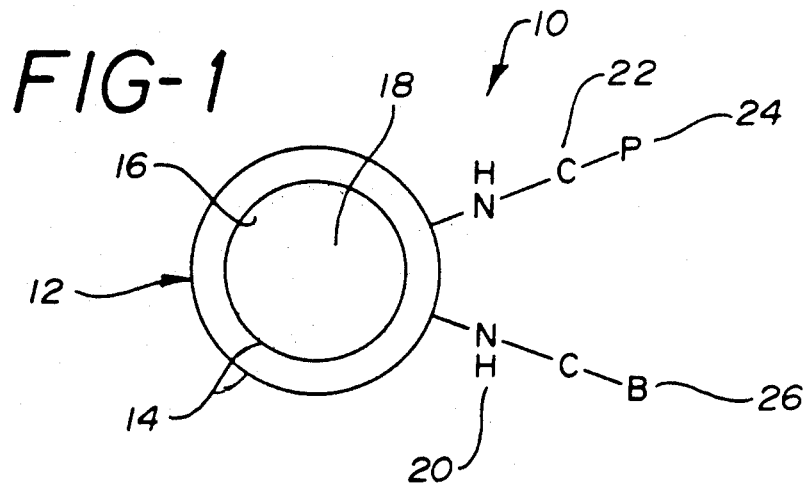

FIG. 1 illustrates a reagent 10 of the invention in its broadest terms. Reagent 10 includes a liposome 12 having a bilayer 14 defining an interior space 16 encapsulating a molecule 18. The liposome surface carries a plurality of amino groups 20 covalently bonded to a plurality of connecting groups 22. A first of the connecting groups is covalently bonded to a ligand molecule 24. A second of the connecting groups is covalently bonded to a charge modifying group 26.

Figure 2:
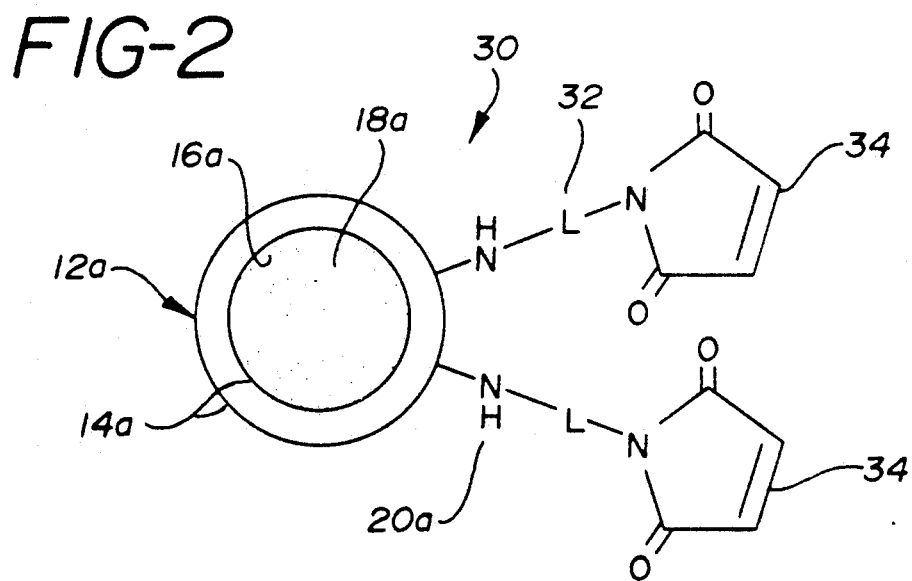

FIG. 2 illustrates an intermediate 30 useful in synthesis of a preferred reagent of the invention. In intermediate 30, amino groups 20a are covalently bonded to a linking group 32 which in turn is covalently bonded to a thiol-reactive group, illustrated in FIG. 2 as a maleimidyl group 34.

Figure 3:
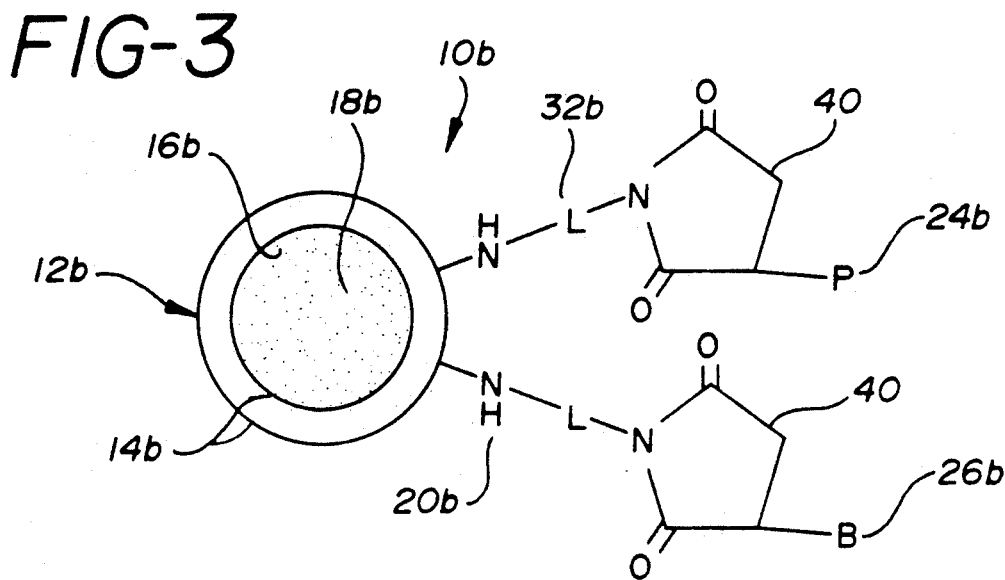

FIG. 3 illustrates a preferred reagent 10b of the invention prepared by reacting maleimidyl groups 34 of FIG. 2 with a thiol containing ligand 24b and with a charge modifying group 26b containing a sulfonate group. It is seen from FIG. 3 that these reactions convert the maleimidyl groups to succinimidyl groups 40. In this disclosure, the term linking group thus defines the portion of the reagent between the amino group on the liposome membrane and the succinimidyl group and the term connecting group defines the linking group in combination with the succinimidyl group.

It is understood that FIG. 2 merely illustrates a preferred intermediate of the invention and is not intended to limit the scope of the invention to the maleimidyl group as the thiol reactive group. Any other thiol-reactive group as known in the art may be used. For example, the thiol reactive group may be a pyridyldithio group or a haloacyl group. A wide variety of liposomes having surface maleimidyl, pyridyldithio and haloacyl substituents conjugated to a nitrogen atom on the liposome surface are disclosed in detail in the aforementioned U.S. Patent Nc. 4,429,008, herein incorporated by reference.

While U.S. Pat. No. 4,429,008 may be referred to for details of the preparation of the thiol reactive intermediate, the following brief description is included in this disclosure as an aid in understanding the principles of the invention.

Liposomes, also referred to as vesicles or sacs, are generally produced from amphiphilic compounds (compounds having both a hydrophobic (nonpolar) portion and a hydrophilic (polar) portion). Most commonly, they are produced by agitation of aqueous dispersions of phospholipids to give either single (unilamellar) or multicompartment (multilamellar) closed bilayers formed from suitably substituted natural or synthetic lipids, preferably phospholipids, as described below. In addition, as known in the art, other components, such as cholesterol may be included in the liposome bilayer.

The substituted phospholipid which may be converted to preferred intermediate 30 by conventional methodology may be synthesized using phosphatidyl ethanolamine (PE), 1, as a representative phospholipid starting material. The amino group of 1

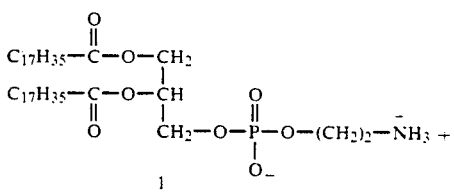

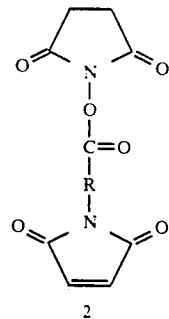

may be reacted with a suitable activated derivative of a maleimidyl reagent, such as active ester 2. In 2 the radical $$C(=O)R$$

corresponds to the linking group 32 of FIG. 2. Representative suitable R groups may be, for example, lower alkylene of about 1 to 10 carbon atoms, branched or unbranched, phenyl or phenylalkylene wherein the alkylene portion may be to about 6 carbon atoms. Particularly preferred active esters for reaction with 1 are given by the following structures 3 and 4 in which the R groups are phenylpropyl and pentamethylene respectively.

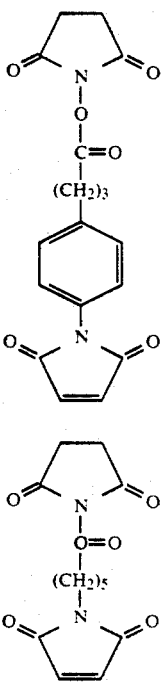

Reaction of maleimidyl active esters 3 and 4 with 1 gives phosphatidyl derivatives 5 and 6 respectively.

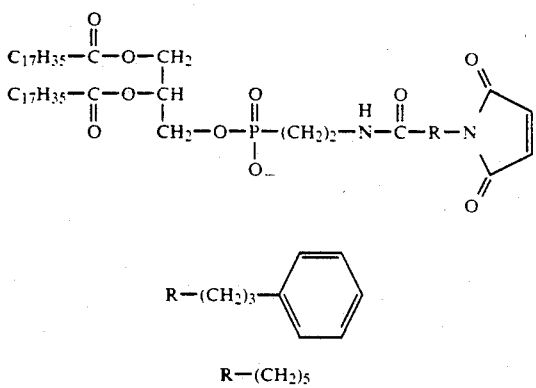

Treatment of aqueous dispersions of 5 and 6 containing a dissolved encapsulant (element 18 in the drawings, described below) under conventional liposome forming conditions gives the intermediate of FIG. 2 wherein the linking group 32 is the unit

C(=O)R defined above.

Formation of liposomes from lipids, including encapsulation of a molecule in the interior thereof, is wholly conventional and fully described in the art, and in view of the detailed disclosure incorporated by reference, no further details with respect to liposome formation is needed for a complete understanding of the invention.

The nature of the encapsulant depends on the intended use of the reagent. Thus, in one application of the reagent, the encapsulant is a therapeutic agent, such as a drug, to be targeted to a specific body location. Liposome mediated drug delivery is conventional.

In the preferred application of the reagent of the invention, the encapsulant is a reporter molecule and the reagent serves as a tracer in an assay, preferably an immunoassay. Thus, the encapsulant may be a radioactive material or an enzyme, such as a hydrolase or a peroxidase. Representative suitable enzymes are alkaline phosphatase and horseradish peroxidase. Assays using radiolabels and enzymes as reporter molecules are conventional in the art.

The most preferred encapsulant is a dye to serve as a reporter molecule. The dye may be an absorbing dye such as, for example, bromosulfophthalein and indocyanine green or preferably a fluorescent dye, such as calcein, phycoerythrin, a lanthanide chelate, fluorescein, of most preferably sulforhodamine B.

The intermediate of FIG. 2 may be converted to the reagent of FIG. 3 by addition of thiols to the maleimidyl groups. Thus, the intermediate may be reacted with a thiol containing ligand, preferably a protein (element 24b) most preferably an antibody or an antibody fragment, such as an Fab' fragment containing a free SH group or a disulfide group reducible to a free SH group. Suitable antibodies which may serve as element 24b are antibodies raised against human chorionic gonadotropin (HCG) and antiviral antibodies such as anti Influenza A, anti respiratory syncytial virus (RSV), anti Herpes simplex virus (HSV), anti adenovirus and anti parainfluenza 3 virus. The most preferred antibody is anti thyroid stimulating hormone (TSH). Conjugation of proteins containing thiols with the thiol reactive liposome may be carried out as described in the aforementioned U.S. Pat. No. 4,429,008.

The choice of thiol containing protein 24b likewise depends on the intended use of the reagent. If the reagent is contemplated to target a therapeutic agent to a specific body location, protein 24b preferably binds to a receptor protein or antigen at the body location. In the preferred application of the reagent of the invention as an immunoassay tracer, protein 24b is the antibody portion of the tracer and thus is chosen to bind immunologically to the assay analyte, usually an antigen.

It is evident that, if any unreacted maleimidyl groups are present on the liposome after addition of thiol-containing protein 24b, these groups, during performance of an assay for an analyte using the reagent as assay tracer, may react nonspecifically with any other nucleophilic group present, such as for example, a thiol or amino group of a capture antianalyte or a component in the buffer matrix. Accordingly, it is conventional to further treat a liposome reagent to insure that no thiol-reactive groups remain on the liposome. As described above, Hatoh et al. discloses improved assay sensitivity by adding various low molecular weight nucleophilic agents subsequent to addition of the thiol-containing protein to inactivate unreacted maleimidyl groups.

In accordance with the present invention, residual thiol-reactive groups, such as the preferred maleimidyl group, are reacted with a sulfonate precursor molecule to introduce charged sulfonate groups onto the liposome surface. In the present disclosure, the term sulfonate precursor is intended to mean any molecule which, on reaction with the thiol reactive group, provides a sulfonate group on the reagent surface. Suitable sulfonate precursors are sulfite or bisulfite ion wherein element 26b of FIG. 3 is SO$_3$X and mercaptosulfonic acids of the structure HS—Y—SO$_3$X wherein 26b is S—Y—

SO₃H and X may be H or alkali metal and Y may be alkyl, aryl, cycloalkyl, aralkyl or heteroalkyl. The term alkyl may be from 1 to about 8 carbon atoms, and representative ring structures are phenyl, benzyl, cyclohexyl, pyridyl, picolyl and oxazinyl.

Reagents including charge modifying groups of the SO₃X type may be prepared by adding sulfite or bisulfite ion to the maleimidyl group, in accordance with the known addition of these reagents to maleimide. Reagents including charge modifying groups of the S—Y—SO₃X type may be prepared by reacting the HS—Y—SO₃X reagents with the maleimidyl group.

Preferred charge modifying groups are sulfite, bisulfite, mercaptopropanesulfonate and mercaptoethanesulfonate.

It is evident that the reagent of the invention may also be prepared by reversing the sequence of thiol additions, i.e., the maleimidyl intermediate of FIG. 2 may first be partially reacted with the sulfonate agent and subsequently with the thiolated antibody. Alternatively, both the thiolated ligand and the sulfonate reagent may be added simultaneously. These sequences provide a reagent having optimal spacing of the surface antibody and sulfonate group and minimize undesirable multipoint attachment of the antibody to the liposome surface. When these sequences are used, it is advisable to complete reagent preparation with a second treatment with the much less expensive sulfonate agent to insure complete inactivation of all maleimidyl groups.

It has been found that submicron particle suspensions of the reagent of the invention are stable (substantially nonaggregating) for months in Tris buffer having a ratio ($\mu$M Pi/mgAb) of about 40 to 80, preferably about 45 to 60 wherein Pi is lipid inorganic phosphate and Ab is antibody. In contrast, aggregation of liposome assay reagents of the prior art occurs within 24 hours as shown in Example X. Aggregation leads to reduced assay specificity or sensitivity particularly for assay reagents contemplated for use after a period of shelf time.

Immunoassays for an analyte using dye- or enzyme-loaded liposomes conjugated to an antianalyte as assay tracer are wholly conventional. Procedures for performing such an assay are fully described in U.S. Pat. No. 4,743,560, the disclosure of which is herein incorporated by reference, and the procedures described therein may be used for an assay using the reagent of the invention.

Another aspect of the invention is a kit of materials for performing an immunoassay for an analyte which includes the reagent of the invention as the assay tracer. Preferred kits include materials for performing a solid phase assay. Thus, the kit includes a solid support coated with an antianalyte and optionally also coated with an inert protein to fill any binding sites on the membrane not occupied by the capture antibody. (In the present disclosure, the term inert protein means a protein which is immunologically unreactive toward any other component of the assay and which does not substantially bind nonspecifically to other proteins in the assay medium, with the understanding that the inert protein may well be immunologically reactive toward other materials which are not part of the assay of the invention.) Representative nonlimiting examples of suitable inert proteins are casein, gelatin and albumin, although others will be evident to those skilled in the art. As is well known in the art, the inert protein serves to avoid or reduce nonspecific binding of other proteins.

Suitable solid supports as known in the art are tubes, wells of a microtiter plate, dipsticks and membranes adapted for conventional flow through assay. The support may be of any suitable material such as glass or preferably plastic. Preferred plastics are polyethylene, polypropylene, polycarbonate, polyvinyl chloride, polyester, nylon, natural rubber, polyacrylate or preferably polystyrene and polyurethane.

The antianalyte may be coated onto the solid support by either absorption or preferably covalent coupling. The antianalyte may be a protein which binds specifically to the analyte and serves to capture the analyte on the support. Thus, when the analyte is an antigen, the antianalyte is a specific binding antibody. Coating of solid supports with antianalytes is conventional in the immunoassay art.

Another component of the kit may be a substrate for an enzyme encapsulated in the liposome of the reagent. Thus, if the enzyme is alkaline phosphatase, suitable substrates are phosphate esters of nitrophenols and indoxyls. If the enzyme is a peroxidase, suitable substrates are diamino benzidine, 5-aminosalicylic acid, o-phenylenediamine and the like. The kit may also include the peroxide required for peroxidase catalyzed oxidation of the substrate, and may include a conventional lysing agent, such as a detergent, to disrupt the liposome and release the enzyme. Selection of a suitable enzyme, substrate therefor and agent for liposome disruption is well within the purview of one skilled in the immunoassay art.

The components of the kit, including the reagent of the invention, may be included individually in the kit or they may be supplied in various combinations either as solutions in an appropriate vehicle such as water or buffer, or in dehydrated or lyophilized form for reconstitution with water or buffer before use. The kit may also include reference standards for the analyte as, for example, one or more analyte samples of known concentration, or it may include other reagents, substrates, or solutions, such as saline or buffers and utensils such as vials or droppers useful in carrying out the assay.

If the solid support is a membrane, it may be provided in an assay device including a housing, preferably plastic, containing a material positioned under the membrane, such as absorbent paper, to facilitate flow of assay liquids through the membranes by capillary action. The housing preferably includes a port to provide access to the membrane. Devices for membrane flow through assay are well known in the art and several are commercially available.

The following examples are provided to further describe the invention but are not to be considered as limitative of the invention.

EXAMPLE I

Liposome Preparation

Liposomes were prepared by the following procedure:

1. To a 2000 ml round bottom rotoevaporator flask, add the following:
   a) 101.8 mg Cholesterol
   b) 188.0 mg Distearoyl Phosphatidyl Choline (DSPC)
   c) 20.6 mg Distearoyl Phosphatidyl Glycerol (DSPG)

d) 8.0 mg crosslinking agent, (Distearoyl Phosphatidyl ethanolaminemaleimidocaproate), (DSPC), DSPE MC e) 14 ml Chloroform 2. Swirl to mix.

3. Place on rotoevaporator with the following settings: Water bath temperature=45° C. Rotation speed=5 rpm 4. Slowly increase vacuum until foaming ceases (approximately 30 min)

5. Reduce pressure and dry lipids to a thin homogeneous film.

6. Dry overnight under vacuum.

7. Add 40 ml of 1mM EDTA buffer, pH 4.5, and swirl at 60° C. for 3 min.

8. Cool in ice water bath.

9. Centrifuge at 4° C. for 30 min.

10. Discard supernatant.

11. Add 40 ml of warm (50° to 52° C.) 0.2M Sulforhodamine B dye to liposome pellet. Mix thoroughly.

12. Extrude the warm lipid/dye mixture through 1.0, 0.4 and 0.2 micron Nucleopore polycarbonate membranes.

13. Chromatograph through a Sephadex G-50, medium, column equilibrated with 50 mM NaOAC buffer, pH 4.5.

14. Determine phosphate concentration.

15. Store at 4° C. until reaction with protein.

EXAMPLE II

Sensitization of Liposomes

The liposomes of Example I were sensitized with thiolated antibody to produce assay tracer by the following procedure.

1. To 4.0 mg protein A purified anti TSH antibody, add 0.2 ml 1M DTT reducing agent in 50 mM NaOAC buffer, pH 6.5.

2. Stir for 45 min at room temperature.

3. Remove DTT by passing the reaction volume over a Sephadex G-50, medium, column equilibrated with 0.1M NaOAC buffer, pH 4.5.

4. Monitor the O.D. at 280 nm and pool antibody fractions (void volume).

5. Mix antibody pool with 180 ml of 1 $\mu$M Pi/ml liposomes of Example I.

6. Adjust pH to 8.0 with 1M Tris buffer.

7. React overnight at room temperature.

8. Centrifuge at 4° C. for 45 min. Discard supernatant.

9. Resuspend pellet in 2 ml of 50 mM Tris buffer, pH 7.4.

10. Chromatograph through a Sepharose Cl-6B column equilibrated with 50 mM Tris buffer, pH 7.4.

11. Centrifuge once again at 4° C. for 45 min.

12. Resuspend pellet in 5 ml of Tris buffer.

13. Determine phosphate concentration and dilute to 1 $\mu$M Pi/ml with 50 mM Tris buffer, pH 7.4.

14. Store at 4° C.

EXAMPLE III

Procedure Used for Post-Treatment of Sensitized Liposomes with 2-Mercaptopropane Sulfonic Acid and 2 Mercaptoethane Sulfonic Acid A. After step 6 of Example II, proceed as follows:

7. React for 5 hours at room temperature.

8. Add 20 $\mu$L of 1M 2-Mercaptopropane propane sulfonic acid and stir at room temperature for 1 hour.

9. Centrifuge at 4° C. for 45 min. Discard supernatant.

10. Resuspend pellet in 5 ml Tris buffer, pH 7.4.

11. Chromatograph through a column of Sepharose CL-6B (40×2.5 cm) equilibrated with 20 mM Tris buffer, pH 7.4.

12. Centrifuge once again at 4° C. for 45 min. Discard supernatant.

13. Resuspend pellet in 5 ml of Tris buffer.

14. Determine phosphate concentration and dilute to 1 $\mu$M Pi/ml with 50 mM Tris buffer, pH 7.4.

15. Store at 4° C.

B. In the same way as A, substitute 1M 2-mercaptoethane sulfonic acid in step 8.

EXAMPLE IV

Procedure Used for Post-Treatment of Sensitized Liposomes with Sodium Bisulfite

After step 6 of Example II, proceed as follows:

7. React for 5 hours at room temperature.

8. Adjust pH to 6.0 with 1N HCl.

9. Add 20 uL of 1M sodium sulfite and stir at room temperature for 1 hour.

10-16. Perform steps 9-15 of Example III.

EXAMPLE V

Procedure Used for Post-Treatment of Sensitized Liposomes with Sodium Sulfite

After step 6 of Example II, proceed as follows:

7. React for 5 hours at room temperature.

8. Add 20 uL of 1M sodium sulfite and stir at room temperature for 1 hour.

9-15. Perform steps 9-15 of Example III.

EXAMPLE VI

Procedure Used for Pre-Treatment of Sensitized Liposomes with Sodium Sulfite

After step 5 of Example II, proceed as follows:

6. Add 15 uL of 0.001M sodium sulfite to 180 ml of MC liposomes (1 $\mu$M Pi/ml), pH 4.5, containing 14.0 mg crosslinker.

7. Allow to stir at room temperature for 2 hours.

8. Add antibody pool to pre treated liposomes.

9. Adjust pH to 8.0 with 1M Tris buffer.

10. React for 5 hours at room temperature.

11. Add 10 uL of 1M sodium sulfite and stir at room temperature for 1 hour.

12-18. Perform steps 9-15 of Example III.

EXAMPLE VII

Procedure Used for Sensitization of Liposomes and Co-Treatment with Sodium Sulfite After step 5 of Example II, proceed as follows:

6. Add 15 uL of 0.001M sodium sulfite to 180 ml of MC liposomes (1 $\mu$M Pi/ml), pH 4.5, containing 14.0 mg crosslinker.

7. Immediately add reduced antibody pool.

8. Adjust pH to 8.0 with 1M Tris buffer.

9. React for 5 hours at room temperature.

10. Add 20 uL of 1M sodium sulfite and stir at room temperature for 1 hour.

11. Centrifuge at 4° C. for 45 min. Discard supernatant.

12. Resuspend pellet in 5 ml Tris buffer, pH 7.4.

13. Chromatograph through a column of Sepharose CL-6B (4×2.5 cm) equilibrated with 20 mM Tris buffer, pH 7.4.

14. Repeat step 11.

15. Repeat step 12.

16. Determine phosphate concentration and dilute to 1 μM Pi/ml with 50 mM Tris buffer, pH b 7.4.

17. Store at 4° C.

EXAMPLE VIII

Procedure Used for Sensitization of Liposomes Co-Treatment with 2-Mercaptopropane Sulfonic Acid After step 5 of Example II, proceed as follows:

6. Add 15 uL of 0.001M 2-Mercaptopropane sulfonic acid to 180 ml of MC liposomes (1 μM Pi/ml), pH 4.5, containing 14.0 mg crosslinker.

7. Immediately add reduced antibody pool.

8. Adjust pH to 8.0 with 1M Tris buffer.

9. React for 5 hours at room temperature.

10. Add 20 uL of 1M sodium sulfite and stir at room temperature for 1 hour.

11. Centrifuge at 4° C. for 45 min. Discard supernatant.

12. Resuspend pellet in 5 ml Tris buffer, pH 7.4.

13. Chromatograph through a column of Sepharose CL-6B (40×2.5 cm) equilibrated with 20 mM Tris buffer, pH 7.4.

14. Repeat step 11.

15. Repeat step 12.

16. Determine phosphate concentration and dilute to 1 μM Pi/ml with 50 mM Tris buffer, pH 7.4.

17. Store at 4° C.

EXAMPLE IX

Procedure Used for Post-Treatment of Sensitized Liposomes with Prior Art Blocking Groups A. In the same way as described in Example III, the sensitized liposomes of Example II were post-treated with DTT.

B. In the same way as described in Example III, the sensitized liposomes of Example II were post treated with cysteine.

EXAMPLE X

Aggregation Studies

Assay reagents of the invention were prepared by the procedures of Examples III-V. Prior art assay reagents were prepared by the procedures of Examples II and IX. The preparations were set aside undisturbed for 24 hours and visually observed for aggregation (extend of clumping at the bottom of the tubes). Aggregation is reported in Table I for representative reagents of the invention. Table II reports direct comparative aggregation data for prior art reagents and reagents of the invention prepared and studied under identical conditions. In the Tables, 0 denotes clear solutions (no aggregation), +1 denotes slight aggregation and +2 to +6 denotes increasing aggregation. Preparations which did not show aggregation at 24 hours were observed for up to 6 months. In general, it was observed that aggregation did not significantly increase after the first 24 hours.

TABLE I

| Reagent Batch | DSPE-MC $mM \times 10^{-4}$ | Pi/Ab | Thiol $mM \times 10^{-6}$ | | | | Ab $mM \times 10^{-6}$ | Aggregation |
|---|---|---|---|---|---|---|---|---|
| | | | a | b | c | d | | |
| 1 | 7.2 | 90 | 2 | | | | 1.8 | +1 |
| 2 | 11.7 | 108 | 4 | | | | 2.3 | 0 |
| 3 | 18.9 | 89 | 4 | | | | 4.7 | 0 |
| 4 | 17.6 | 81 | 5 | | | | 2.3 | 0 |
| 5 | 3.0 | 75 | 2 | | | | 0.87 | 0 |
| 6 | 3.4 | 65 | 2 | | | | 0.87 | +1 |
| 7 | 3.9 | 65 | 50 | | | | 2.1 | +1 |
| 8 | 7.8 | 75 | 50 | | | | 2.0 | 0 |
| 9 | 4.8 | 50 | 30 | | | | 2.1 | +1 |
| 10 | 10.4 | 52 | 10 | | | | 2.0 | 0 |
| 11 | 10.6 | 75 | 20 | | | | 3.0 | 0 |
| 12 | 9.3 | 70 | 40 | | | | 2.9 | 0 |
| 13 | 9.3 | 75 | 20 | | | | 2.7 | +1 |
| 14 | 11.7 | 70 | 40 | | | | 3.5 | 0 |
| 15 | 3.9 | 40 | 75 | | | | 2.3 | +5 |
| 16 | 2.0 | 38 | 20 | | | | 1.0 | +6 |
| 17 | 4.1 | 50 | | 5 | | | 1.9 | 0 |
| 18 | 4.1 | 50 | | | | 5 | 1.9 | 0 |
| 19 | 3.6 | 45 | 5 | | | | 1.9 | 0 |
| 20 | 3.6 | 45 | 10 | | | | 1.9 | 0 |
| 21 | 3.2 | 40 | | 5 | | | 1.9 | 0 |
| 22 | 3.8 | 46 | | | | 5 | 1.9 | 0 |
| 23 | 11.6 | 60 | | 5 | | | 4.7 | +6 |
| 24 | 8.3 | 71 | | 5 | | | 2.8 | +3 |
| 25 | 18.8 | 89 | 4 | | | | 4.7 | 0 |
| 26 | 11.5 | 108 | 4 | | | | 2.3 | 0 |
| 27 | 17.2 | 81 | 5 | | | | 2.3 | 0 | a ... mercaptopropane sulfonic acid
b ... mercaptoethane sulfonic acid
c ... sodium sulfite
d ... sodium bisulfite

TABLE II

| Reagent Batch | DSPE-MC $mM \times 10^{-4}$ | Pi/Ab | Thiol $mM \times 10^{-4}$ | | | | Ab $mM \times 10^{-6}$ | Aggregation |
|---|---|---|---|---|---|---|---|---|
| | | | a | c | d | e | f | |
| 28 | 5.7 | 40 | 10 | | | | 1.5 | +1 |
| 29 | 5.7 | 40 | | | 10 | | 1.5 | +1 |

TABLE II-continued

| Reagent Batch | DSPE-MC mM × 10⁻⁴ | Pi/Ab | Thiol mM × 10⁻⁴ a | c | d | e | f | Ab mM × 10⁻⁶ | Aggregation |
|---|---|---|---|---|---|---|---|---|---|
| 30 | 5.7 | 40 | 10 | | | | | 1.5 | 0 |
| 31 | 5.7 | 40 | | | 10 | | | 1.5 | +3 |
| 32 | 5.7 | 40 | | | | 10 | | 1.5 | +3 |
| 33 | 5.7 | 40 | | | | | | 1.5 | +2 | e...DTT
f...cysteine

It is seen from Tables I and II that the reagents of the invention show either no aggregation or slight aggregation. In contrast, Table II shows that, under identical conditions of preparation and study, reagent batches 31 and 32 having an overload $10 \times 10^{-4}$ mM) show even higher aggregation than batch 33 having no blocking group.

Reagent batches 15 and 16 which showed extensive aggregation have ratios of 40 or less. The results obtained with reagent batches 23 and 24 are considered to be anomalies.

EXAMPLE XI

In the same way as described in Example II, the liposomes of Example I are sensitized with antibodies raised against Influenza A virus (Flu A), human chorionic gonadotropin (HCG) respiratory syncytial virus (RSV), Herpes simplex virus (HSV), adenovirus and parainfluenza 3 virus. The sensitized liposomes are then posttreated with 3-mercaptopropane sulfonic acid, sodium bisulfite and sodium sulfite as described in Examples III, IV and V to give reagents of the invention which are useful as tracers in assay for HCG, and antigens of RSV, HSV, adenovirus and parainfluenza 3 viruses.

What is claimed is:

1. An assay reagent comprising:
   a) a liposome bearing a plurality of surface amino groups;
   b) a plurality of linking groups covalently bonded to said amino groups;
   c) a plurality of succinimidyl groups covalently bonded to said linking groups;
   d) a protein covalently bonded to a first of said succinimidyl groups through a sulfur atom of said protein;
   e) a charge modifying group covalently bonded to a second of said succinimidyl groups, said charge modifying group being selected from the group consisting of the structures SO3R and S—Y SO3R wherein R is H or alkali metal ion and Y is selected from the group consisting of alkyl, aryl, cycloalkyl, aralkyl and heteroalkyl wherein the term alkyl is from 1 to 8 carbon atoms; and
   f) a reporter molecule occluded in said liposome.

2. The reagent of claim 1 wherein said linking group is selected from the group consisting of an acyl, aroyl, hetaroyl, heteroalkyl and aralkyl group.

3. The reagent of claim 2 having from 1 to 10 carbon atoms in said linking group.

4. The reagent of claim 1 wherein said protein is selected from the group consisting of an antibody and an antibody fragment.

5. The reagent of claim 4 wherein said antibody is selected from the group consisting of anti human chorionic gonadotropin, anti thyroid stimulating 6. The reagent of claim 1 wherein said reporter molecule is selected from the group consisting of a dye and an enzyme.

7. The reagent of claim 6 wherein said dye is selected from the group consisting of an absorbing dye and a fluorescent dye.

8. The reagent of claim 6 wherein said enzyme is selected from the group consisting of a hydrolase and a peroxidase.

9. An assay reagent comprising
   a) a lipsome bearing a plurality of surface amino groups;
   b) a plurality of connecting groups covalently bonded to said amino groups;
   c) a ligand covalently bonded to a first of said connecting groups through a sulfur atom of said ligand;
   d) a charge modifying group covalently bonded to a second of said connecting groups, said charge modifying group being selected from the group consisting of the structures SO3R and S—Y SO3R wherein R is H or alkali metal ion and Y is selected from the group consisting of alkyl, aryl, cycloalkyl, aralkyl and heteroalkyl wherein the term alkyl is from 1 to 8 carbon atoms; and
   e) a molecule occluded in said liposome.

10. The reagent of claim 9 wherein said ligand is a protein.

11. The reagent of claim 9 wherein said connecting group includes a thiol reactive group.

12. The reagent of claim 11 wherein said thiol reactive group is selected from the group consisting of a maleimidyl, pyridyldithio and haloacyl group.

13. The reagent of claim 9 wherein said molecule is selected from the group consisting of a radiolabel, a dye and an enzyme.

14. An assay reagent comprising:
   a) a liposome having a surface bearing a plurality of amino groups;
   b) a plurality of succinimidylcaproamide groups bonded to said surface, said amino groups providing the nitrogen atom of said amido groups;
   c) an anti thyroid stimulating hormone antibody covalently bonded to a first of said succinimidylcaproamide groups through a sulfur atom of said antibody;
   d) a charge modifying group covalently bonded through a sulfide sulfur atom to a second of said succinimidylcaproamide groups, said charge modifying group being selected from the group consisting of the structures SO3R and S—Y SO3R wherein R is H or alkali metal ion and Y is selected from the group consisting of alkyl, aryl, cycloalkyl, aralkyl and heteroalkyl wherein the term alkyl is from 1 to 8 carbon atoms; and
   e) a fluorescent dye encapsulated in said liposome.

15. A kit of materials for performing an assay for an unknown quantity of analyte in a liquid comprising an assay tracer comprising the reagent of claim 1 and a solid support having coated thereon an antianalyte.

16. The kit of claim 15 wherein said analyte is an antigen, said antianalyte is a first antibody specific to said antigen and said protein portion of the reagent is a second antibody specific to said antigen.

17. The kit of claim 15 further comprising an inert protein attached to said support.

18. The kit of claim 15 wherein said reporter molecule is an enzyme and the kit further comprises a substrate for said enzyme and a lysing agent for said liposome.

19. The kit of claim 15 wherein said reagent is in a lyophilized form.

20. The kit of claim 15 wherein said reagent is in an aqueous solution.

21. The kit of claim 15 further comprising a reagent selected from the group consisting of a buffer and saline.

22. The kit of claim 15 further comprising at least one liquid containing analyte of known concentration.

23. The kit of claim 15 further comprising a liquid substantially free of analyte.

24. The kit of claim 15 wherein said support is a membrane.

25. The kit of claim 24 further comprising a housing said membrane therein, said membrane being positioned over an absorbent material, said housing including a port to give access to said membrane.

* * * * *

UNITED STATES PATENT AND TRADEMARK OFFICE
CERTIFICATE OF CORRECTION

PATENT NO. : 5,248,590

DATED : September 28, 1993

INVENTOR(S) : Rutner et al

It is certified that error appears in the above-indentified patent and that said Letters Patent is hereby corrected as shown below:

On the title page, item [21] Appl. No.: "333,937" should read --733,937--.

Signed and Sealed this

Twenty-sixth Day of April, 1994

Attest:

BRUCE LEHMAN

*Attesting Officer*　　*Commissioner of Patents and Trademarks*